(12) United States Patent
Owen

(10) Patent No.: US 11,609,204 B2
(45) Date of Patent: Mar. 21, 2023

(54) CARBON DIOXIDE AND/OR HYDROGEN SULPHIDE DETECTION SYSTEM AND METHOD AND USE THEREOF

(71) Applicant: Blue Unit A/S, Odense (DK)

(72) Inventor: David Alexander Owen, Søndersø (DK)

(73) Assignee: Blue Unit A/S, Odense (DK)

( * ) Notice: Subject to any disclaimer, the term of this patent is extended or adjusted under 35 U.S.C. 154(b) by 509 days.

(21) Appl. No.: 16/635,494

(22) PCT Filed: Aug. 1, 2018

(86) PCT No.: PCT/EP2018/070893
§ 371 (c)(1),
(2) Date: Jan. 30, 2020

(87) PCT Pub. No.: WO2019/025501
PCT Pub. Date: Feb. 7, 2019

(65) Prior Publication Data
US 2020/0371058 A1    Nov. 26, 2020

(30) Foreign Application Priority Data

Aug. 4, 2017  (DK) .......................... PA 2017 70601

(51) Int. Cl.
*G01N 27/27*       (2006.01)
*G01N 21/3504*     (2014.01)
(Continued)

(52) U.S. Cl.
CPC ......... *G01N 27/27* (2013.01); *G01N 21/3504* (2013.01); *G01N 21/85* (2013.01);
(Continued)

(58) Field of Classification Search
CPC .. G01N 33/18; G01N 33/1893; G01N 33/182; G01N 33/0044; G01N 33/004;
(Continued)

(56) References Cited

U.S. PATENT DOCUMENTS 5,643,799 A  *  7/1997  Atwater ............... G01N 33/182
                                                      436/178
5,902,751 A     5/1999  Godec et al.
(Continued)

FOREIGN PATENT DOCUMENTS

DE        2854447 A1     6/1980
EP        1043585 A2 *  10/2000   ............. G01N 27/40
(Continued)

OTHER PUBLICATIONS

K Balogh et al: "Characterization of a novel dissolved CO2 sensor for utilization in environmental monitoring and aquaculture industry", Proceedings of SPIE, vol. 8785, Nov. 18, 2013 (Nov. 18, 2013), 1000 20th St. Bellingham WA 98225-6705 USA, pp. 8785FC-8785FC-7, XP055524743, ISSN: 0277-786X, ISBN: 978-1-5106-2011-7, DOI: 10.1117/12.2027518.
(Continued)

*Primary Examiner* — Nathaniel J Kolb
(74) *Attorney, Agent, or Firm* — Dykema Gossett PLLC

(57) ABSTRACT

Various embodiments of the present disclosure are directed to carbon dioxide and/or hydrogen sulphide sampling and detection system and method for determination of the content of gaseous CO2 and/or H2S in a liquid, among other chemical compounds. In one embodiment, the detection system includes a membrane block having a liquid sample inlet port and a sample outlet port between which a sample flow path extends. The membrane block includes a first membrane unit and a second membrane unit. The first membrane unit includes a sample flow on the first side of a
(Continued)

first permeable membrane element, and a carrier gas flow on the second side of the first permeable membrane element. The second membrane unit having a sample flow on the first side of a second permeable membrane element and a carrier gas flow on the second side of the second permeable membrane element.

18 Claims, 9 Drawing Sheets

(51) Int. Cl.
    *G01N 21/85* (2006.01)
    *G01N 27/40* (2006.01)
    *G01N 27/413* (2006.01)
    *G01N 33/00* (2006.01)
    *G01N 33/18* (2006.01)

(52) U.S. Cl.
    CPC ........... *G01N 27/40* (2013.01); *G01N 27/413* (2013.01); *G01N 33/004* (2013.01); *G01N 33/0044* (2013.01); *G01N 33/182* (2013.01); *G01N 33/1893* (2013.01)

(58) Field of Classification Search
    CPC ...... G01N 27/413; G01N 27/40; G01N 21/85; G01N 21/3504; G01N 27/27
    See application file for complete search history.

(56) References Cited

U.S. PATENT DOCUMENTS

| 2010/0070201 A1 | 3/2010 | Bell et al. |
| 2016/0206993 A1 | 7/2016 | Deng |

FOREIGN PATENT DOCUMENTS

| EP | 1043585 A2 | 11/2000 |
| EP | 2423677 B1 | 4/2009 |
| WO | 199528626 A1 | 10/1995 |
| WO | 9721096 A1 | 6/1997 |
| WO | 2007092665 A2 | 8/2007 |
| WO | 2014121169 A1 | 8/2014 |

OTHER PUBLICATIONS

M. Mirfendereski et al: "Investigation of H2 S and CO2 Removal from Gas Streams Using Hollow Fiber Membrane Gas-liquid Contactors", Chemical and Biochemical Engineering Quarterly., vol. 31, No. 2, Jul. 7, 2017 (Jul. 7, 2017), CR, pp. 139-144, XP055523830, ISSN: 0352-9568, DOI: 10.15255/CABEQ.2016.1022.

* cited by examiner

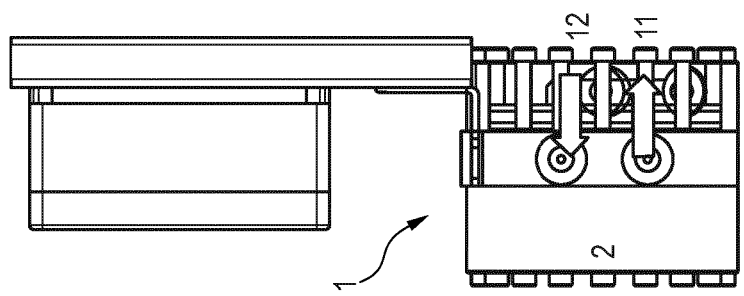
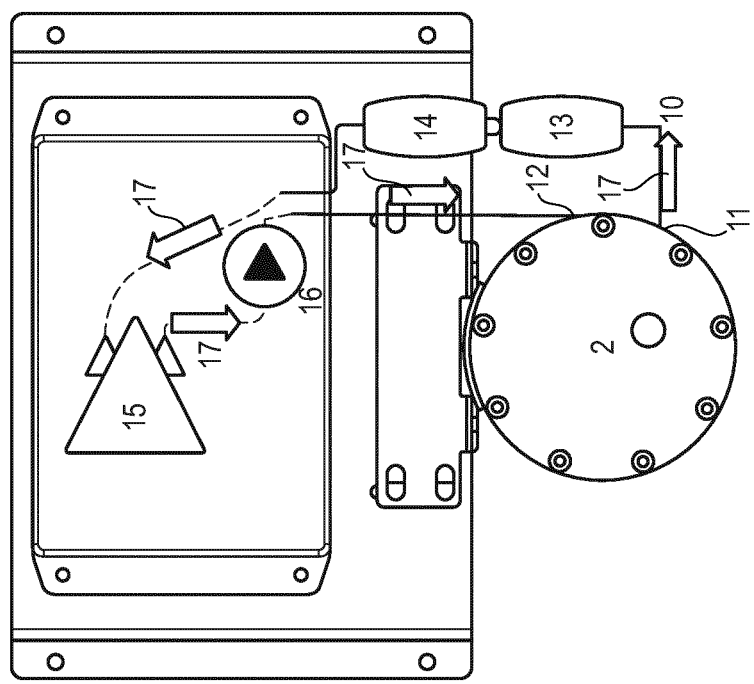
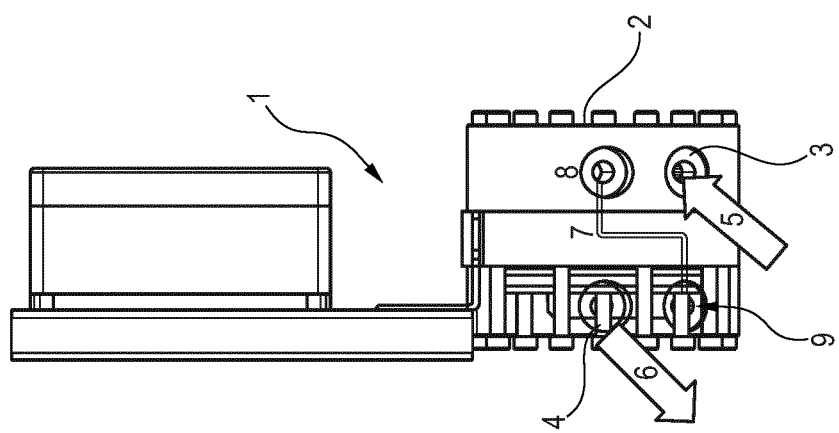

CARBON DIOXIDE AND/OR HYDROGEN SULPHIDE DETECTION SYSTEM AND METHOD AND USE THEREOF

CROSS-REFERENCE TO RELATED APPLICATIONS

This application is a national stage filing based upon International PCT Application No. PCT/EP2018/070893, filed 1 Aug. 2018, which claims the benefit of priority to Denmark application No. PA 2017 70601, filed 4 Aug. 2017.

FIELD OF THE INVENTION

The present invention relates to a carbon dioxide and/or hydrogen sulphide sampling and detection system for determination of the content of gaseous CO2 and/or H2S in liquids, in particular aqueous liquids, and/or for the detection of the total carbonate content in aqueous liquids, wherein said CO2 and/or H2S sampling and detection system comprises a membrane block having a liquid sample inlet port and a sample outlet port between which a sample flow path extends.

The present invention also relates to a carbon dioxide and/or hydrogen sulphide sampling and detection method.

BACKGROUND OF THE INVENTION

Fish today are increasingly cultured in land based recirculation aquaculture systems (RAS). To ensure optimal fish performance in terms of growth rate, feed conversion and fish welfare, it is critical to ensure a stable water quality. Central to stable water quality in fish tanks is understanding the carbonate buffer system.

Fish blood is pH 7.4 and so the fish can become stressed if pH deviates too far from this level or is unstable. For pH stability, alkalinity is critical. Alkalinity is the water's ability to react and neutralise acid. Fish farm alkalinity is dominated by the soluble bases within the carbonate buffer system-primarily bicarbonate ($HCO_3^-$).

The carbonate buffer system is illustrated below.

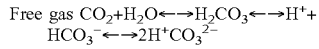

Free gas $CO_2 + H_2O \leftrightarrow H_2CO_3 \leftrightarrow H^+ + HCO_3^- \leftrightarrow 2H^+ CO_3^{2-}$ Biological processes acidify the fish farm, meaning $H^+$ ions are produced and pH begins to decrease. The greater the concentration of bicarbonate and carbonate anions will mean less pH decreases caused by biological activity.

As the pH drops on a fish farm, the carbonate buffer system is driven to the left yielding greater amounts of toxic free CO2 gas. Many studies indicate that if free CO2 is too high (e.g. >20 mg/l for trout), then fish cannot excrete CO2 effectively, lowering blood pH and their ability to transport oxygen.

The ability to measure the carbonate buffer system of a fish farm (primarily free CO2 and $HCO_3^-$) provides some important advantages for management. Firstly, understanding free CO2 gas concentrations is important as levels above 10-20 mg/L are directly toxic to the fish.

Understanding $HCO_3^-$ concentrations means alkalinity can be managed to a level where pH fall across the fish tank can be minimized. Remember, a pH drop across the fish tank means the carbonate buffer system is driven to the left yielding greater amounts of toxic free CO2 gas. As the concentration of $HCO_3^-$ will determine how much free CO2 is finally yielded at a given pH, $HCO_3^-$ concentration must not come too high either!

Understanding $HCO_3^-$ levels, before and after water treatment filters/degassers is also critical for the mass balance calculations required to assess efficiency of a system. Only is this way can the water treatment filter/degasser be safely managed.

Only CO2 gas is measured today in fish farming. CO2 probes today are slow, taking generally up to 15-20 minutes for a single measurement. Furthermore, once a sample has been made, at least further 10 minutes is required for the sensor to fall to zero again, before a new measurement can be made without the risk of a previous measurement affecting the new result. Thus, these probes are typically installed in a single location of a fish farm, and simply allowed to monitor this single location continuously.

Intensive biological activity around a fish farm can mean significant and sudden pH drops, with the carbonate buffer system being driven to the left yielding greater amounts of the toxic free CO2 gas. This results in greatly variable levels of free CO2 gas around a single fish farm, demanding improved and more encompassing systems for measurement of free CO2.

The prior art CO2 detection systems have several disadvantages.

Firstly, common CO2 gas measuring systems use a single membrane across which free CO2 gas in the liquid sample is collected into a closed loop gas flow. The closed loop gas flow is circulated to a CO2 sensor which detects the amount of CO2 in the circulating gas.

As an example, if a tank 1 had a high free CO2 content of 20 mg/L and tank 2 had a free CO2 content of 10 mg/L, one has to expect about one hour for measuring two tanks, because it would take around 15 minutes to read 20 mg/L, then a stabilizing period of about 10-30 minutes before the sensor is a sufficiently low level to measure a significantly lower level, and finally around 15 minutes to read 20 mg/L of the second sample.

This is a very slow procedure, why there is a desire for improvements.

Secondly, the process of stabilizing the carbon dioxide probe between measurements is commonly a very slow process. This means that an earlier measurement can affect the following measurement if an insufficient stabilizing period is not given resulting in incorrect measurements that cannot be relied upon.

Thirdly, common carbon dioxide probes have a CO2 sensor that becomes very hot during operation. This implies that moisture that normally is generated at the air-to-water interface of the probe evaporates into the air. However, when the CO2 sensor after a measurement cools down, when powered off, moisture condenses from the air to form large droplets. When the probe is powered up again subsequently, this moisture enters to the sensor head, causing damage to some sensor head types, and/or providing erroneously high values in other sensor head types.

In WO 2007092665 is disclosed a carbon dioxide detection system for determination of the content of CO2 in aqueous liquids. The CO2 detection system comprises a membrane unit having a liquid sample inlet port and a sample outlet port between which a sample flow path extends. The membrane unit comprises a membrane element which has a sample flow on a first side of the membrane element and a carrier gas flow on a second side of the membrane element. An infrared sensor is located in the carrier gas flow path.

Thus, it is desirable to provide a system and method that improves the speed of CO2 measurements, in particular for in-line use. Further it is desirable to improve reliability of CO2 measurements and reduce cross over influence on CO2 detection levels from a preceding sample to a subsequent sample. Thirdly, it is desirable to provide a CO2 detection system which uses CO2 detection sensors which have reduced tendency of becoming hot and cause the above mentioned problems and systems has the advantages of a centralized measurement system but not the disadvantages of the prior art.

It is noted that the present invention is in the following described in relation to CO2 and/or total carbonate detection in water samples from aqua culture systems, such as fish tanks for breeding fish in land based fish farms. The present invention is, however, not restricted to be used in aqua culture systems, but is equally applicable for detection of CO2 gas content in liquids/water/aqueous environments and/or total carbonate in liquid samples or alkalinity relating to the carbonate content is relevant as control parameter from other sources where frequent and/or in-line detection of CO2 and/or total carbonate is required or desired.

Such other applications may include the food or pharmaceutical processing industry, in particular food processing that involves fermentation processes, e.g. brewing of beer, wine or the like or other food or pharmaceutical producing processes that in-wolves fermentation to obtain a final product.

Other relevant uses may be within the waste water treatment facilities, potable, demineralized and/or (ultra) pure water production.

Further it is believed that the present invention is also applicable for detection of carbon dioxide in gas flows. The invention would in particular be applicable for detection of CO2 in gas streams having a relatively high degree of humidity or steam content or wet gas streams that are saturated with water vapour or steam.

Hydrogen sulphide (H2S) another gas that mays cause problems in aqua cultures. H2S is typically generated during biological purification, e.g. in biofilters, H2S is generated from sulphate ions ($SO_4^{2-}$) by sulphate reducing bacteria present in the biofilm/biomass of the biological water purification plant, in particular during anoxic or anaerobic cycles.

Seawater contains significant amounts of sulphates. In aqua cultures breeding seawater species of fish, shellfish or crustaceans (in the following just called fish) in onshore ponds or fish tanks where the water is purified and recycled to the fish ponds/tanks are thus in a high risk of generating H2S and exposing the fish during water purification cycles. H2S may also be generated in fresh water aquacultures, e.g. because unused fish feed and/or fish feces adds sulphates to the water in the fish ponds/tanks.

The risk of upregulating the growth of sulphate reducing bacteria is especially pronounced in low nitrate periods. This may elevate the H2S concentration in recycled, purified water or seawater. This may cause elevated risks for H2S concentration in agricultures using seawater.

H2S is toxic to fish. H2S it is toxic when present in concentrations from about 15 μg/l or above depending on the species of fish.

The H2S content depends on the pH and can be lowered by increasing PH or by adding oxidizing agents, such as ozone, oxygen and/or nitrates. At pH of 7 approximately 50% of all Sulphide ions are present as H2S. By increasing pH to e.g. 7.5 the H2S level can be lowered significantly.

Currently, inline detection of H2S in aqueous environment is complicated and prone to inaccuracies and/or failure. Currently available H2S detection systems usually comprises a H2S electrode arranged directly and locally in the fish tanks/pond. These H2S detections suffer from the same drawbacks as described in relation to prior art CO2 detection systems discussed above.

Object of the Invention

The object of the present invention is to provide an in-line carbon dioxide and/or hydrogen sulphide probe system that is designed for rapid and reliable determination of the carbon dioxide content and/or the total carbonate content and/or H2S content in liquid samples, in particular aqueous samples.

The object of the invention is also to provide a method and carbon dioxide and/or hydrogen sulphide detection system is particularly useful for determining CO2 and/or H2S in water in ponds, such as fish tanks or ponds of land based fish farms, irrespective of whether they contain fresh water, brackish water or sea water.

The object of the invention is to also provide a method and carbon dioxide and/or hydrogen sulphide detection system that allows for high measurement speed, and a rapid turn-around between measurements.

Another object of the invention is making the CO2 and/or H2S detection system and method significantly faster than current technologies.

Another object of the invention is to protect the sensor head from condensation, but also allows the probe to rapidly drop to a near zero CO2 and/or H2S levels between measurements, providing a rapid turn-around between measurements.

Another object of the invention is to provide a method for measuring CO2 and/or any bound carbonate forms and/or H2S in aqueous samples.

Description of the Invention

The present invention relates to a carbon dioxide and/or hydrogen sulphide sampling and detection system for determination of the content of gaseous CO2 in liquids, in particular aqueous liquids, and/or for the detection of the total carbonate and/or the H2S content in aqueous liquids, wherein said CO2 and/or H2S detection system comprises a membrane block having a liquid sample inlet port and a sample outlet port between which a sample flow path extends. Said membrane block comprises a first membrane unit having a sample flow on the first side of a first permeable membrane element and a carrier gas flow on the second side of the first permeable membrane element. Said membrane block further comprises a second membrane unit having a sample flow on the first side of a second permeable membrane element and a carrier gas flow on the second side of the second permeable membrane element. Said first and second membrane units are arranged in series in the liquid sample flow path. The gas flow path is a closed loop that includes gas circulation means, the second gas containing side of the first and second membrane units. The system further comprises a carbon dioxide gas sensor and/or a hydrogen sulphide detection unit, which is arranged in the closed loop gas circulation flow path.

This system provides an in-line carbon dioxide and/or hydrogen sulphide detection system that is designed for rapid and reliable determination of the carbon dioxide content and/or the total carbonate content and/or hydrogen sulphide content in liquid samples, in particular aqueous samples. The membrane block is able to isolate CO2 and/or H2S in gas form from the liquid sample and allow for determination of the content of CO2 and/or H2S in gas phase.

This system also provides an in-line H2S detection system that is designed for rapid and reliable determination of the H2S content in liquid samples, in particular aqueous samples. The membrane block is also able to isolate H2S in gas form from the liquid sample and allow for determination of the content of H2S in gas phase.

Thus, the sampling and detection system of the present invention can be used for the detection of H2S instead of or together CO2 system by merely substituting the CO2 sensor with a H2S detection unit.

In addition, CO2 and H2S can both be sampled and isolated from the sample in the membrane block and then detected by arranging a CO2 sensor and a H2S detection unit in series in the closed gas flow loop.

Thus, this system also provides an in-line H2S detection system that is designed for rapid and reliable determination of the H2S content alone, or together with CO2, in liquid samples, in particular aqueous samples. The membrane block is able to isolate H2S in gas form from the liquid sample and allow for determination of the content of H2S in gas phase.

In the following, when mentioning carbon dioxide —CO2— this description equally applies to the detection of H2S unless otherwise specified.

The application of multiple membranes that allow for free CO2 and/or H2S gas to be driven from the water sample to an air/gas loop faster than in prior art systems. This is the key to making the sensors significantly faster than current technologies.

The carbon dioxide detection system is particularly useful for determining CO2 in water in ponds of land based fish farms. It can measure directly free CO2 gas, and/or any bound carbonate forms. For fish farms, the carbonates are primarily HCO3—. The design of the CO2 detection system has allowed for high measurement speed, and a rapid turn-around between consecutive measurements. It is also applicable as an in-line system, where water can be pumped through the probe, rather than hanging in a tank. The combination of measurement speed, rapid turn-around and the in-line configuration, make it ideal for measurement of many places across a single fish farm or similar applications.

The system comprises a membrane block with a liquid sample inlet and a liquid sample outlet. The membrane block comprises a first and a second membrane unit as mentioned above, each having a liquid flow path side and a gas loop side. The first and second membrane units are preferably arranged on top of each other with the gas flow paths towards the centre of the membrane block.

The liquid sample flow, i.e. mostly aqueous liquids, may be subjected to filtration prior to introduction into the membrane block in order to remove any particulate matter present in the sample flow. This reduces or event eliminates the risk of fouling in the membrane units. Filtration may be applied prior to any further pre-treatments, such as addition of acids to the liquid sample flow, which is discussed further below.

In addition, initial removal of free bubbles, e.g. air bubbles, present in the liquid may be carried out using a closed container with airspace in which free bubbles in the sample flow may be collected, and by extracting the liquid sample flow from the bottom of the container.

The outlet of liquid sample side of the first membrane unit is connected to the inlet of the liquid side of the second membrane unit to provide a serial connection of the membrane units. The connection and second membrane units are connected with a hose, tube or pipe connection arranged exteriorly or interiorly in the membrane block.

The liquid sample passing through liquid sample flow path is introduced into the first membrane unit and then spreads evenly across the liquid side of the first membrane. The CO2 and/or H2S gasses diffuses through the membrane to a gas loop. Transfer of gaseous CO2 and/or H2S across the membrane is mainly driven by the gas partial pressure gradient across the membrane. The gas transfer is thus driven towards an equilibrium as defined by Henry's Law. This ensures fast stabilisation of the CO2 and/or H2S gas concentration in the gas flow.

The pressure in the liquid sample flow is preferably raised about 100-300 mbar relative to atmospheric pressure, or more preferred 150-250 mbar relative to atmospheric pressure or more preferred 200 mbar relative to atmospheric pressure. The pressure in the liquid sample flow is preferably minimized.

Alternatively, the liquid samples are sucked through the sample flow path by means of a vacuum pump provided at or downstream to the sample outlet of the membrane block. This reduces the pressure in the liquid sample flow to slightly below atmospheric pressure, e.g. 50-25 mbar below atmospheric pressure, without causing significant reduction of the transfer of gas across the membranes in the membrane block.

The air pressure in the air loop varies with the content of CO2, H2S and/or ambient air in the sample. Usually, the pressure in the air loop is only raised slightly above to atmospheric pressure during measurements, such as between 20-60 mbar relative to atmospheric pressure, but may be quite variable.

In each of the membrane units, the membrane is preferably supported by a membrane support member to provide stability. The membrane support member is preferably provided on the gas flow side of the membrane. The membrane support member is preferably a mesh element, a grate or a perforated plate.

Next, the liquid sample is transferred to the second membrane unit again spreading evenly across the membrane and again with gas diffusion. CO2 and/or H2S gas can diffuse either way across the membranes.

The liquid sample leaves the membrane block via the outlet. The outlet from the second membrane unit is thus also the liquid sample outlet of the membrane block.

On the gas side of each membrane support member in the first and the second membrane units, a gas collection chamber is provided. The gas collection chamber covers substantially the entire gas flow side of the membrane. The height of the gas collection chamber above the membrane surface is small relative to the diameter/diagonal of the membrane. Thus, the gas collection chamber may be described as dish shaped. The dish shape is provided to ensure that the CO2 and/or H2S gas that diffuses through the membrane is easily admixed into the body of gas by providing a maximised surface relative to volume in the gas collection chamber, whereby the above mentioned equilibrium in CO2 and/or H2S gas diffusion across the membranes is obtained quickly.

The gas circulates flows initially from the gas collection chamber in the first membrane unit, then to the gas collection chamber in the second membrane unit. From the gas collection chamber of the second membrane unit, the gas continues to flow into the CO2 gas sensor and/or the H2S detection unit. The CO2 gas sensor and the H2S detection unit are discussed in further detail below. Then the gas is circulated back to the gas collection chamber of the first membrane unit.

An air pump is provided in the gas loop to circulate the gas in the loop. This ensures effective circulation of the gas and results in that the above mentioned equilibrium on CO2 concentration/partial pressure across the membranes is obtained faster, which also results in that reliable results on the CO2 content in the liquid samples are obtained faster than in previous techniques.

The carrier gas, which circulates in the closed gas flow loop, is usually atmospheric air because this is a cheap solution and atmospheric air is easily provided in the gas loop, e.g. by means of the breather valve arrangement as discussed further below. Other carrier gasses may be applied as carrier gasses in the gas loop in special situations. Such alternative carrier gases are gases that do not interfere with CO2 measurements in the CO2 gas sensor, and may e.g. be pure nitrogen.

The carbon dioxide and/or hydrogen sulphide sampling and detection system preferably includes that the first and second permeable membrane elements are hydrophobic membranes. Hereby is obtained that CO2 gas and/or H2S gas is able to pass through the permeable membranes while water vapour, or at least the majority thereof, is retained on the liquid side, i.e. the sample side, of the membrane. This reduces the risk for condensation of water vapour in the CO2 sensor and thus further reduces the risk that the CO2 sensor provides faulty results as discussed below. In addition, the risk is reduced in relation to damage occurring to the CO2 sensor as a result of condensation of water vapours and/or water ingress in the CO2 sensor as described above in relation to the prior art.

The preferred hydrophobic membranes are selected from the group consisting of polytetrafluorethylene (PTFE) or polydimethylsiloxane (PDMS) membranes, or combinations thereof.

The preferred membranes have a pore size of less than 10 microns or most preferred less than 0.02 microns, because this pore size reduces the transfer of water/water vapour across the membranes.

The preferred CO2 sensor is a CO2 gas sensor that detects an absorption of gaseous CO2 in the infra red (IR) spectrum, because these sensors represent a low risk of being damaged because of ingress of condensed water as discussed above. Other commercially available CO2 gas sensors may also be equally applicable. For example, electrochemical measuring cells that contain an electrolyte, can be used to generate an electric signal proportional to a sample gas.

When using a CO2 gas sensor based on IR technology, condensation does not damage the sensor as in older technologies. However, excessive condensation can lead to too high results of CO2 detected by the sensor.

CO2 gas sensors based on IR technology uses detection of CO2 gas absorption spectrum of IR radiation. Such sensors are standard equipment within determination of the content of CO2 in air, but so far they do not appear to have been in use in systems for detection of CO2 gas and or Carbonates in liquids, in particular aqueous liquids, for example fish tank water.

The IR spectrum of carbon dioxide has a strong absorption band consisting of many overlapping peaks. This band is caused by unsymmetrical C=O stretching, is placed at 2300 cm-1 corresponding to a wavelength of 4.3 µm. Thus it is possible to detect CO2 gas and determine the concentration in the gas in the gas loop by means of the CO2 gas sensor.

The H2S gas detection unit comprises a commercially available electrochemical measuring cell. This measuring cell contains an electrolyte, a measuring electrode (anode), a counter electrode (cathode) and a reference electrode. Gas that reaches the sensor passes initially through a capillary opening and then diffuses through a hydrophobic barrier, and eventually reaches the electrode surface. This allows for the correct amount of gas to react at the sensing electrode to produce a sufficient electrical signal while preventing the electrolyte from leaking out of the sensor. An electric signal proportional to the pollutant is produced in the measuring cell. This electric signal is amplified and used for the measurement.

A low concentration gas sensor with high sensitivity is applied. It combines a less restricted capillary opening, and a coarsely porous hydrophobic barrier to allow more gas molecules to pass through to produce enough signal for better sensitivity.

The preferred H2S detection unit comprises a sensor unit and a transmitter unit. The sensor unit is arranged in the gas loop. A distribution cap is preferably provided around the sensor unit. The distribution cap comprises an inlet and an outlet to which the gas loop is connected so as to ensure equal distribution of the gas flow over the sensor unit. The distribution cap is preferably attached to the sensor unit in air tight manner.

As the capillary barrier is less restricted, a safety valve (opening at preferably 200 mBar above atmospheric pressure) is preferably installed in the gas loop to manage a constant air pressure at the capillary opening.

The H2S detection unit has a lower detection limit corresponding to 1 µg H2S/l water in sample flow. The upper detection limit is corresponding to 250 µgH2S/l water in sample flow, i.e. well above the toxic concentration level of H2S as discussed above.

Reduction of condensation of water vapour in the gas flow loop is managed by a combination of hydrophobic membranes, preventing water and/or water vapours from entering to the gas loop as described above.

If the sample and detection unit is installed in an environment with high humidity in the ambient air, the air used in the gas loop may be dried. The air drying means may comprise a compressor to increase the pressure and drive the air through a humidity absorbing sorbent. Preferably, the sorbent used is also able to absorb any CO2 present in the ambient air. Suitable sorbents used for dehumidifying air and removal of CO2 from ambient air are commercially Examples of suitable commercially available sorbents are e.g. molecular sieve beaded media. These commercially available molecular sieves are e.g. provided in beaded form and are frequently used in pressure swing adsorption systems. Molecular sieves act as the effective adsorbents for various liquids and gases, and is good for carbon dioxide removal As an of example a suitable commercially available molecular sieve 13× molecular sieve beaded media provided by Puregas (www.airdryers.com).

In addition, condensation of water in the sensor is reduced or avoided by regular flushing of the gas loop with fresh atmospheric air or carrier gas by using the breather valves arrangement, as described below. The arrangement of these is designed to also allow for any condensation that may have accumulated inside the air loop to be driven out, using the force of gravity and the flow of the air.

Therefore, the gas circulation loop comprises a breather valve arrangement comprising two serially connected three way valves between the CO2 gas sensor and/or H2S detection unit and the atmosphere.

The breather valves are preferably a set of magnetic valves or other equally applicable valves. The set of three way valves are preferably provided between the gas outflow from the membrane block and the CO2 sensor in the gas flow loop. The set of three valves enable flushing of the gas loop with new atmospheric air from the outside environment.

This protects the sensor head from condensation, but also allows the probe to rapidly drop to a near zero CO2 level between measurements, providing a rapid turn-around between measurements. A near zero CO2 level between measurements is important to ensure an earlier measurement does not impact upon a future measurement.

Common carbon dioxide probes have a CO2 sensor that becomes very hot during operation. This implies that moisture that normally is generated at the air-to-water interface of the probe evaporates into the air. However, when the CO2 sensor after a measurement cools down, when powered off, moisture condenses from the air to form large droplets. When the probe is powered up again subsequently, this moisture enters to the sensor head, causing damage. Especially, the process of stabilizing the carbon dioxide probe between measurements is commonly a very slow process. This means that an earlier measurement can affect the following measurement if an insufficient stabilizing period is not given. The problem with damage caused by ingress of humidity exists to a lesser degree in the H2S detection unit due to a hydrophobic barrier before the gas enters to the electrodes of the sensor.

As an example, if a fish tank had a high free CO2 content of 20 mg/L it would take around 15 minutes to read 20 mg/L, then a stabilizing period of about 10 minutes before the CO2 sensor is at a sufficiently low level to measure a new sample correctly without any carry-over contamination of CO2 gas in the gas loop from the former sample measurement. The same would apply for H2S sensors mounted locally in fish tanks.

This is a very slow procedure, why there is a desire for improvements.

During normal measurement operation, the 3-way valve combination is not activated. This means the circulating gas in the gas loop simply flows through the valves with no connection with the outside environment. The system is a closed gas loop during measurements.

An improvement is achieved with the above mentioned carbon dioxide sensor combined with the breather valve arrangement. The breather valve arrangement that provides the CO2 sensor with the possibility for opening the loop to the atmosphere (or another carrier gas as discussed above) and flush the gas loop with atmospheric air by means of the air pump sucking in atmospheric air into the gas loop via one three way valve and to expel the circulating CO2 rich gas from the gas loop via the second three way valve when both valves are opened. Using such a breather valve assembly as described above, results in that the process of stabilizing the carbon dioxide probe between measurements is very fast. A stabilizing period of about 3 seconds to get the probe back to a zero level may be obtained, which is extremely fast. Thus, instead of the prior art 10 minutes stabilizing period, the intermediate period is reduced to three seconds, which is almost instantly.

The carbon dioxide and/or hydrogen sulphide sampling and detection system may further comprise a mixer station for admixing one or more acids into the liquid flow.

This enables faster and more reliable results when detecting CO2/carbonate content and/or H2S content dissolved in an aqueous liquid sample because the amount of CO2 present in the liquid water sample.

Another important function of the CO2 probe is the ability to measure the entire carbonate buffer system concentration, i.e. total carbonate, of a fish farm (primarily free CO2 and $HCO_3^-$). To do this acid is added to the water sample to measure any bound carbonate forms. As the sensor head is designed to read only free CO2 gas, a small dose of an acid to lower the pH value of the water sample to below pH 4, drives the carbonate buffer system completely to the left as shown in the reaction scheme mentioned in the introductory part of the description. Hereby nearly all carbonates dissolved in the aqueous liquid sample becomes free CO2 gas which can be measured by the CO2 sensor in the gas loop. The final measurement is effectively the concentration of CO2 and HCO3— together. As mentioned above, the free CO2 may initially be determined in a sample followed by acidification of a part of the same sample and thus also determining the concentration's dissolved carbonates. The combined amount of free CO2 and dissolved carbonates then represent the total carbonate content in the sample.

The results from the sensor are transferred to a datalogger or may be transferred to a controller which controls process parameters for the environment from which the sample is collected, e.g. a fish tank in a fish or any of the other possible applications mentioned above and further below. The controller may e.g. be a programmable logic controller (PLC).

Acid addition to the liquid sample is preferably controlled by a programmable logic controller (PLC). A pH sensor may provide information to the controller on the resultant PH in the liquid sample and thus control addition of acid to a PH below 4.

Addition of acid to the liquid sample is effected by directing the aqueous liquid sample to a mixing block. This can be accomplished by a set of bypass valves that direct the liquid sample to the mixing block when activated. When bypass valves are activated an acid dosing pump is also activated. The acid pump doses the acid, such as citric acid, from an acid reservoir to the liquid aqueous sample in the mixing block whereby pH of the aqueous liquid sample rapidly drops to below pH 4 in order to be able to detect total carbon content of the sample. When detecting (also) H2S the pH is lowered to about 3 The aqueous liquid sample is then transferred to a reaction chamber to ensure a residence time that enables HCO3— to chemically change to become free CO2 gas. The aqueous liquid sample is then directed to the CO2 detection system described above for detection of free CO2 and carbonates, which are now present as CO2 gas in the sample.

In a variant of the CO2 and/or H2S sample and detection system two sample and detection lines each with membrane block and a gas loop with sensors/detection units. These are arranged in parallel. A first sample and detection line comprises a CO2 sensor and bypasses the mixing block. The first line thus detects free CO2 in the aqueous liquid sample.

The second sample and detection line receives comprises a CO2 sensor and a H2S detection unit in the gas loop. The membrane block receives an acidified sample flow with lowered pH, e.g. below 3, from the mixing block as described above.

The mixing block may further contain a heater, e.g. arranged in the sample flow path or in the reaction chamber, to heat the aqueous liquid sample prior to forwarding the sample to the membrane block. The heating can be carried out before, during or after addition of acid. Alternatively, the aqueous liquid sample is heated without the addition of acid during its passage through the mixing block.

H2S solubility in water depends on the water temperature. At increasing water temperatures, the H2S gas more easily extracted/released from the aqueous phase and transferred to the gas phase. Therefore, when detecting H2S (alone or in combination with total carbon, the liquid sample flow is preferably heated to 25-45° C. to increases the diffusion velocity of CO2 through the membrane and thus equilibrium is obtained faster.

Thus, the second sample flow to the second line of the dual line system mentioned above is additionally further heated to 25-45° C. This decreases the solubility of CO2 and especially H2S whereby the gasses are faster and more easily released from the liquid flow and transferred across the membranes to the gas loop.

When preparing the acidified sample flow in the bypass before sending the acidified sample flow into the membrane block, a much faster process is obtained and more reliable results are obtained in subsequent measurements because the risk of left over acid in the sample flow path is reduced significantly when adding acid to the sample flow in the bypass only.

The sample preparation by acidification is preferably made during the period where free CO2 is measured in the CO2 detection system or alternatively during the period where the gas circulation loop is flushed as described above as well as below.

When the bypass valves remain deactivated, the aqueous liquid sample can flow through them directly to the CO2 system for detection of any unbound CO2 present in the aqueous liquid sample.

In the CO2 detection system the high level of free CO2 in the samples enables a rapid diffusion across the CO2 sensor membrane and thus is easier to determine total carbonate contents compared to detecting only free CO2 in the aqueous liquid sample.

The carbon dioxide and/or hydrogen sulphide sampling and detection system is in a variant built into a portable unit.

Hereby it becomes possible to perform faster and very reliable determination of CO2 dissolved carbonates and/or total carbonate content and/or hydrogen sulphide content in aqueous liquids anywhere on a production site where it is advantageous to be able to monitor.

This portable unit, e.g. within an enclosure, may then contain the detection system mentioned above with the membrane block and the gas loop with the CO sensor. In addition the portable unit may further contain the sample preparation system including optional filters for removing particulates prior to measurements of CO2, sample acidification means as described above and possibly an internal or external acid reservoir. In addition, the portable unit comprises a power source, e.g. a battery and/or a plug/cord for connecting to a standard 110 V or 220 V electrical power supply. A data communication means may also be included to provide data to another unit, e.g. a controller, computer or the like. The data communication may be a wired connection or wireless connection, e.g. radio frequency, mobile phone communication, wireless network, e.g. Wi-Fi, or Bluetooth connection, and/or communication via the internet.

The system described above is equally applicable in determination and/or monitoring the hydrogen sulphide content in aqueous liquid samples and is equally applicable for inline measurements using a hydrogen sulphide gas sensor instead of the CO2 gas sensor as described above. The H2S gas dissolves in water where it is in equilibrium with HS-ions.

Thus the present system is also ideal for determination of the content of hydrogen sulphide in aqueous liquid samples and only requires another sensor in the gas loop or it may be the same sensor as for CO2 measurements. In the membrane block, the hydrogen sulphide diffuses across the membranes as described above for CO2 gas.

The liquid sample flow path and/or the membrane block may comprise a heater element to increase the liquid sample temperature and/or maintain constant elevated temperatures within the sample flow and/or within the membrane units in the membrane block. This increases the diffusion velocity of CO2 through the membrane and thus equilibrium is obtained faster. Further, the increased temperature pushes the equilibrium towards CO2 being in gas form.

The preferred temperature range in which the CO2 detection system works is by providing a liquid sample flow temperature of to 25-35° C., or preferably around 30° C. and/or maintaining the temperature in the membrane block at 25-35° C., or preferably around 30° C. because this increases the diffusion velocity of CO2 through the membrane.

The objects and advantages of the system as already discussed above are also met by a method for sampling and detection of carbon dioxide and/or hydrogen sulphide for the determination of the content of gaseous CO2 and/or H2S in liquids, in particular aqueous liquids, and/or for the detection of the total carbonate content in aqueous liquids, comprising the steps of isolating gaseous CO2 and/or H2S from the liquids, in particular aqueous liquids in a membrane block by a sample flow liquid passing through the membrane block, by passing the gaseous CO2 and/or H2S contained in the sample flow through first and second permeable membrane element in first and second membrane units of the membrane block and into a closed gas flow loop, while maintaining the sample liquid flow in the sample flow path, where said first and second membrane units have a sample flow on the first side of a first and second permeable membrane element and a carrier gas flow on the second side of the first and second permeable membrane element, and said first and second membrane units are arranged in series in the liquid sample flow path, and wherein the gas flow path is a closed loop where the gas is circulated through the membrane units and to a carbon dioxide gas sensor, which is arranged in the closed loop gas circulation flow path.

Preferably, the closed loop gas circulation flow path flows through the first and second membrane units in counter-current direction relative to the liquid sample flow.

This provides a faster diffusion of CO2 and/or H2S gas through the membrane and thus ensures that the equilibrium partial pressure of CO2 in the gas loop is reached faster. The reason is that the CO2 partial pressure and/or H2S partial pressure in the gas that enters the gas side of the membrane units in the membrane block is lower than in the gas that exits the membrane block. The CO2 gas and/or H2S gas content in the sample in the liquid flow path is high when it enters and low when it exits. Thus providing flow in counter current ensures that more CO2 gas and/or H2S gas diffuses across the membrane and thus that the equilibrium partial pressure of CO2 and/or H2S is reached faster.

Alternatively, in a less preferred variant, the closed loop gas circulation flow path flows through the first and second membrane units in concurrent direction relative to the liquid sample flow.

The method for sampling and detection of carbon dioxide preferably further comprises adding one or more acids to the aqueous liquid sample for setting free carbon dioxide from the aqueous liquid sample prior to measuring the free carbon dioxide and thereby obtaining a measure for the total carbonate concentration in the aqueous liquid sample.

Hereby it becomes possible to measure any bound carbonate forms. As the sensor head is designed to detect only free $CO_2$ gas, a small dose of acid to the water sample to reduce pH to below 4, drives the carbonate buffer system completely to the left by means of the acid mixing block etc. as described above. This ensures that nearly the entire carbonate content in the sample becomes free $CO_2$ gas. The final measurement is effectively the sum of the concentration of $CO_2$ and $HCO_3-$ together.

In one variant the method comprises a first step of introducing a liquid sample into the membrane block that is not acidified whereby the free $CO_2$ present in the liquid sample is detected. In a second measurement, a similar sample is acidified and introduced into the membrane block whereby the concentration of carbonates present in the liquid sample is determined. In this way the free $CO_2$ content as well as the carbonates and/or $H_2S$ can be determined.

In principle any strong or medium strong acid can be used for acidifying the liquid sample, provided that the acid can lower the sample pH to below 4. Suitable acids include organic and/or inorganic acids, with the exception of carbonic acids. Preferred acids are non-toxic organic acids such as citric acids, malic acid, tartaric acid and/or inorganic acids such as hydrochloric acid, sulphuric acids and/or phosphoric acid and/or mixtures thereof provided that they are compatible with the materials that are in contact with the liquid sample on the liquid sample side of the membranes in the membrane block.

Preferably, the method includes raising the temperature of the liquid sample flow to 25-45° C., such as 25-35° C. or preferably around 30° C. and/or maintaining the temperature in the membrane block at 25-35° C., or preferably around 30° C. because this increases the diffusion velocity of $CO_2$ and/or $H_2S$ through the membrane.

In addition, initial removal of free bubbles may be carried out using a closed container (not shown in drawings) with an airspace in which free bubbles in the sample flow may be collected, and by extracting the liquid sample flow from the bottom of the container.

As mentioned above, the gas circulation loop preferably comprises a breather valve arrangement comprising two three-way valves, which are connected in series. The breather valve arrangement is preferably arranged in the gas loop arranged between the $CO_2$ gas sensor and/or the $H_2S$ detection unit and the gaseous side of the membrane block gas flow path, between the $CO_2$ gas sensor/$H_2S$ detection unit and an air pump, or between the air pump and an air inlet to the membrane block, and wherein the method comprises opening the breather valve arrangement between subsequent measurements for providing a connection from the gas flow path to ambient atmosphere, allowing humidity to leave the $CO_2$ sensor and/or for venting the gas present in the closed loop gas circulation flow path to the atmosphere prior to a subsequent measurement of carbon dioxide.

Thus, the gas loop preferably includes the $CO_2$ gas sensor and/or $H_2S$ detection unit, which is provided in combination with a breather valve arrangement as already described above. The breather valve arrangement in a closed state separates the $CO_2$ sensor and the gas loop from atmospheric air (or another carrier gas source) and which in an open state provides a passage from the $CO_2$ sensor and the gas loop to atmospheric air.

The method comprises providing a sample of the water and measuring the amount of free carbon dioxide with a $CO_2$ sensor, and/or detecting $H_2S$ with a $H_2S$ detection unit; then opening a breather valve arrangement to open a path between the $CO_2$ sensor/$H_2S$ detection unit and atmospheric air and thereby evaporating possible moisture from the $CO_2$ sensor into air, then closing the breather valve arrangement again. Then, a new liquid sample may be introduced into the membrane block for a subsequent carbon dioxide or total carbonate measurement with the $CO_2$ sensor in the gas loop and/or a $H_2S$ measurement with the $H_2S$ detection unit. For example, the time in which the breather valve arrangement is open is less than 1 minute. Thus, the time between measurements can be correspondingly reduced to this time of less than 1 minute. Reference is also made to the description of these features above in relation to the system.

As mentioned above, the $CO_2$ detection and monitoring system is particularly suitable for monitoring $CO_2$ gas, dissolved carbonate, total carbonates and/or $H_2S$ gas in water in fish tanks or ponds in fish farms. Therefore, the present invention also provides a fish farm comprising a $CO_2$ and/or $H_2S$ detection and monitoring system as described above and/or below.

As mentioned above, the $CO_2$ and/or $H_2S$ detection and monitoring system is particularly suitable for monitoring $CO_2$ gas, dissolved carbonate and/or total carbonates and/or $H_2S$ gas in other applications. Thus, the present invention also includes use of the system according to any or the method for determining the carbon dioxide content in a liquid broth, such as in pharmaceutical production processes, food or feed preparation processes, or similar processes that involves a fermentation processes and/or water treatment processes.

DESCRIPTION OF THE DRAWING

The present invention will in the following be described in more detail with reference to the figures in which FIGS. 1a-1c show the $CO_2$ or $H_2S$ detection system according to the present invention from one side, from above and from the opposite side.

DETAILED DESCRIPTION OF THE INVENTION

Figure 2B:
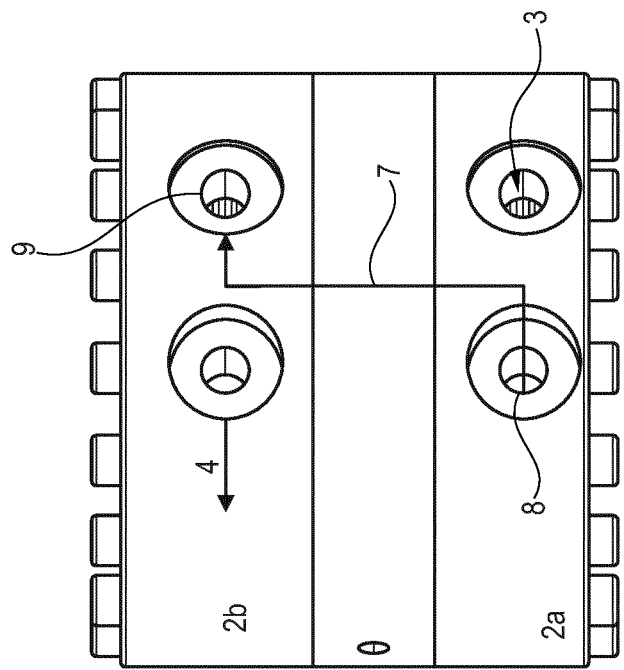
FIG. 2b is a side view of the membrane block with the liquid flow ports of the first and second membrane units.

FIG. 1a-1c shows the main components of the carbon dioxide and/or hydrogen sulphide detection and monitoring system 1. The carbon dioxide and/or hydrogen sulphide detection and monitoring system 1 for liquid aqueous samples is designed initially to extract CO2 gas and/or H2S gas out of a liquid sample flow to a gas loop 10. This is achieved in the membrane block 2.

Initially, the liquid flow sample is filtered in a (not shown) filter unit in order to remove any particulate matter. Any standard particulate filter screen would be applicable as long as it is able to remove particles down to a size of approx. 10 μm.

In addition, initial removal of free bubbles may be carried out using a closed container (not shown in drawings) with an airspace in which free bubbles in the sample flow may be collected, and by extracting the liquid sample flow from the bottom of the container.

The membrane block 2 comprises a liquid sample flow inlet 3 and a liquid sample flow discharge port 4. The liquid sample flow direction is illustrated by the arrows 5,6 in FIG. 1a.

The membrane block 2 comprises two separate membrane units 2a, 2b. The membrane units 2a, 2b are arranged in series by providing a flow connection 7 between an outlet port 8 of the first membrane unit 2a with an inlet port 9 of the second membrane unit 2b.

The gas flow loop 10 has gas flow outlet 11 from the gas side 21 of the membrane 19 in the first membrane unit 2a of the membrane block 2. The gas loop 10 further has an inlet 12 to the gas side 21 of the membrane 19 in the second membrane unit 2b.

From the gas flow outlet 11 of the membrane block 2, the gas flow circulates through the gas loop 10.

The breather valve assembly comprising a first 13 and a second three-way valve 14 are included in the gas flow between the gas flow outlet 11 and the CO2 sensor 15. Alternatively, if the system is used for H2S detection only, then a H2S detection unit 29 (not shown in FIG. 1) is provided instead of the CO2 sensor 15.

An air pump 16 is arranged on the downstream side of the sensor 15 as shown in FIG. 1b. The air pump 16 may, however, in alternatives be installed upstream of the sensor 15 or between the gas flow outlet 11 from the membrane block and the valve 13.

Alternatively, the breather valve assembly may be arranged between the air pump 16 and the sensor 15, or between the air pump 16 and the membrane block gas flow inlet 12.

The liquid sample flow inside the membrane block 2 (see FIG. 2a) is spread evenly across a hydrophobic membrane 19 on the liquid flow path 18 in the first membrane unit 2a. The gas diffuses through the membranes to the gas loop 10, driven by the gas partial pressure gradient towards equilibrium as per Henry's Law. The liquid sample flow then passes through the tube connection to the liquid flow path 18 in the second membrane unit 2b again spreading evenly across the second hydrophobic membrane 19 in the second membrane unit 2b, again with gas diffusion across the membrane. CO2 gas and/or H2S gas can diffuse either way across the membranes.

The pressure in the liquid sample flow is preferably raised about 100-300 mbar relative to atmospheric pressure, or more preferred 150-250 mbar relative to atmospheric pressure or more preferred 200 mbar relative to atmospheric pressure.

Preferably, the pressure in the liquid sample flow is preferably minimized. Indeed the liquid can be sucked through the membrane block 2 using a vacuum pump arranged at the liquid sample outlet of the membrane block 2. This reduces the pressure in the liquid sample flow to slightly below atmospheric pressure, e.g. 50-25 mbar below atmospheric pressure, without causing significant reduction of the transfer of gas across the membranes in the membrane block.

The air pressure in the air loop varies with the content of CO2 and/or H2S gas in the sample. Usually, the pressure in the air loop is only raised slightly above to atmospheric pressure during measurements, such as between 20-60 mbar relative to atmospheric pressure, but may be quite variable.

Each membrane sits on a membrane support 20, such as a plate, mesh or grate, which is arranged on the gas side of the membranes 19 within the gas loop. Below each membrane support 20 is a low height disc shaped gas collection chamber 21 on the gas side of the membrane 19. The gas loop flow initially enters a gas flow inlet 12 and passes through gas collection chamber 21 on the gas side of the membrane 19 in the second membrane unit 2b. From the gas collection chamber 21 on the gas side of the membrane 19 of the second membrane unit 2b, the gas flow passes to the gas collection chamber 21 on the gas side of the membrane 19 in the first membrane unit 2a, via a not shown gas flow connection conduit. The flow then exits the membrane block 2 via the gas flow outlet 11 and to the first 3-way magnetic valve 13, then to the second 3-way magnetic valve 14. From the second 3 way valve 14, the gas flow enters into the CO2 gas 15 H2S gas sensor (not shown but arranged instead of CO2 sensor 15). Finally the gas flow passes through to the air pump 16, that drives the gas back to the membrane block gas flow inlet 12 on the gas flow side 21 of the second membrane unit 2b.

Figure 6:
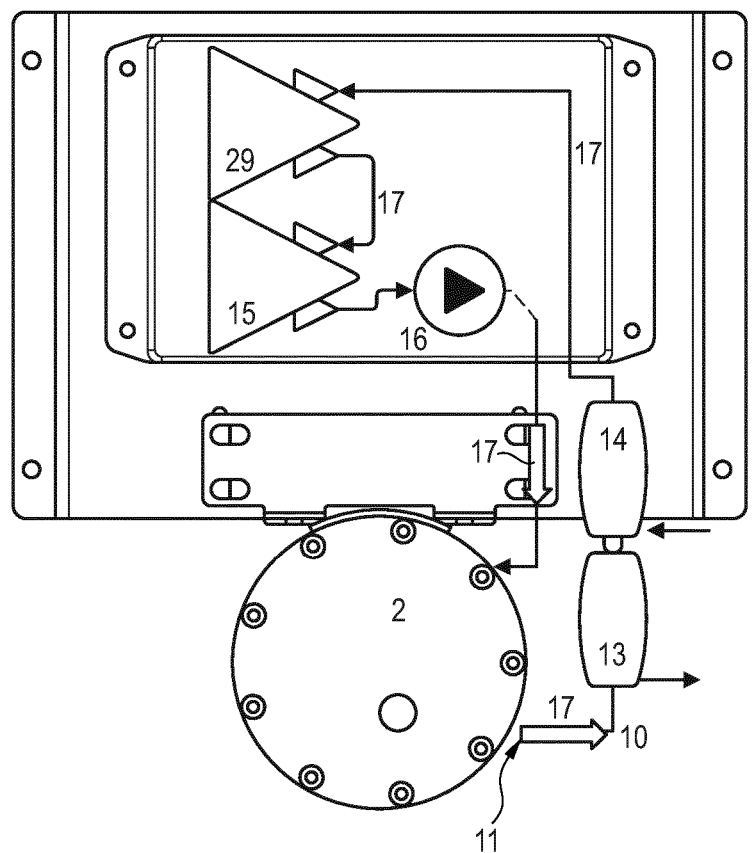
FIG. 6 shows a combined $CO_2$ and $H_2S$ detection system according to a variant of the present invention seen from above.

In a variant shown in FIG. 6, in which both CO2 or total carbonate as well as H2S is detected, the air loop passes from the second 3-way valve 14, the gas flow enters into the H2S detection unit 29, followed by the CO2 gas sensor 15. Finally the gas flow passes through to the air pump 16 that drives the gas back to the membrane block gas flow inlet 12 on the gas flow side 21 of the second membrane unit 2b.

Otherwise the system shown in FIG. 6 is in principle identical to the system shown in FIG. 1b.

The liquid sample flow path and/or the membrane block may comprise a heater element (not shown) to increase the liquid sample temperature and/or maintain constant elevated temperatures within the sample flow and/or within the membrane units.

Preferably, the heating element is arranged in the liquid sample flow path 22 through the mixing block 25 or in the reaction chamber 27 so as to heat the aqueous liquid sample prior to passing the sample to the membrane block 2.

The CO2 gas sensor 15 uses infrared technology as described above, so condensation does not damage the sensor as in older technologies. However, excessive condensation can lead to too high results. Condensation is managed by a combination of hydrophobic membranes 19, preventing water vapour from entering to the gas loop 10, and by regular flushing of the gas loop with atmospheric air from the outside environment using the breather valve assembly represented by the two 3-way valves 13,14. See FIG. 3. During the flushing sequence, the first and second 3 way valves 13, 14 are both activated while leaving the air pump 16 on.

The H2S gas detection unit 29 detects H2S gas in the gas loop, Any commercially available H2S gas detector/sensor that is applicable for detection of H2S in gaseous environments can in principle be used.

The preferred H2S detection 29 unit uses an electrochemical measuring cell. This measuring cell contains an electrolyte, a measuring electrode (anode), a counter electrode (cathode) and a reference electrode. An electric signal proportional to the pollutant combination is produced in the measuring cell. This electric signal is amplified and used for the measurement. The measuring cells use the capillary diffusion barrier technology. The use of capillary diffusion barrier technology and an additional temperature compensation avoid a negative effect caused by fluctuating air pressure and temperature.

Figure 8:
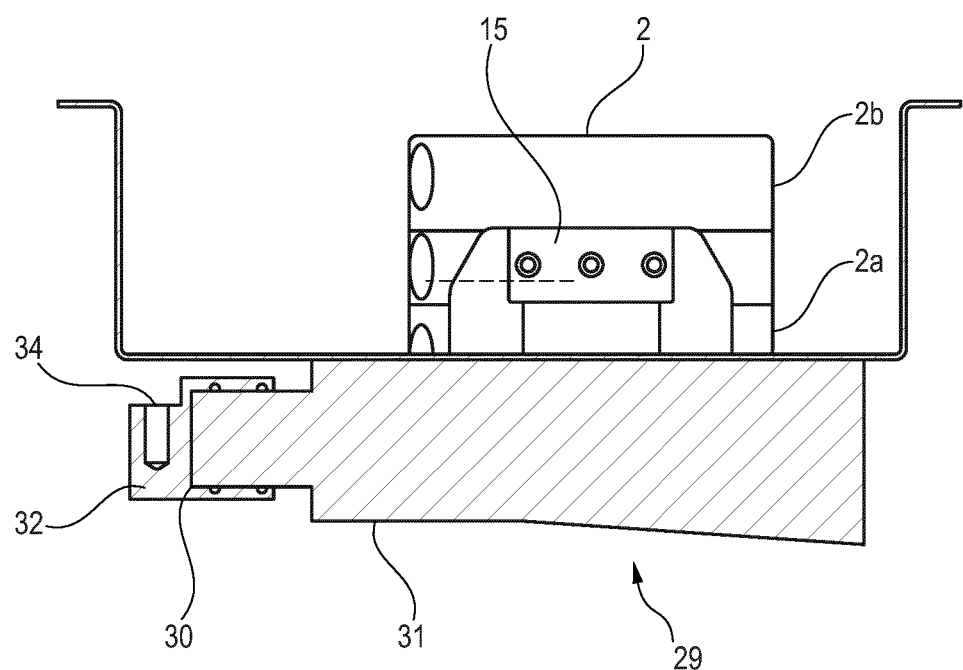
FIG. 8 shows the arrangement of a $H_2S$ detection unit in a gas loop, where the $H_2S$ sensor is provided with a distribution cap, and FIG. 9 graph from the tests performed in example 4.

The H2S detection unit comprises a sensor unit 30 and a transmitter unit 31 (see FIG. 8). The sensor unit 30 of the H2S detection unit 29 is arranged in the gas loop. A distribution cap 32 is provided around the sensor unit 30, preferably in air tight manner. The distribution cap 32 comprises an inlet 33 and an outlet 34 to which the gas loop is connected.

The H2S detection unit 29 is arranged in the gas loop to substitute the CO2 sensor 15 shown in FIG. 1 when only H2S gas is to be detected.

FIG. 6 shows a possible arrangement of the gas loop where the H2S detection unit 29 is arranged in series with the CO2 sensor 15. The H2S detection unit 29 can be arranged upstreams to the CO2 sensor 15 as shown in FIG. 6, or alternatively, the H2S detection unit 29 is arranged downstreams of the CO sensor 15.

Flushing the gas loop 10 using the 3-way valve combination (FIG. 3) is also important to allow the CO2 gas partial pressure in the gas loop to rapidly drop to a near zero CO2 level between measurements. This provides a rapid turnaround between measurements. This also avoids that CO2 gas present in the gas loop 10 from one sample measurement is carried over in the next sample measurement and thus provides false results.

Zero CO2 gas level in the gas loop 10 corresponds to average CO2 gas concentration in atmospheric air. At present approximately atmospheric $CO_2$ concentration has a level around 400 parts per million. Clean atmospheric air does in general not contain any traceable amounts of H2S.

A near zero CO2 and/or H2S gas level between measurements is important to ensure an earlier measurement does not impact upon a future measurement. An earlier measurement may for example be very high, as compared to the next coming measurement. Without the ability to flush the gas loop of the old sample air, then the CO2 and/or H2S in the gas loop would need to diffuse across the membrane back to the water, again driven by the gas partial pressure gradient towards equilibrium as per Henry's Law. As the gradient difference is often not large, this is a slow process.

Figure 3:
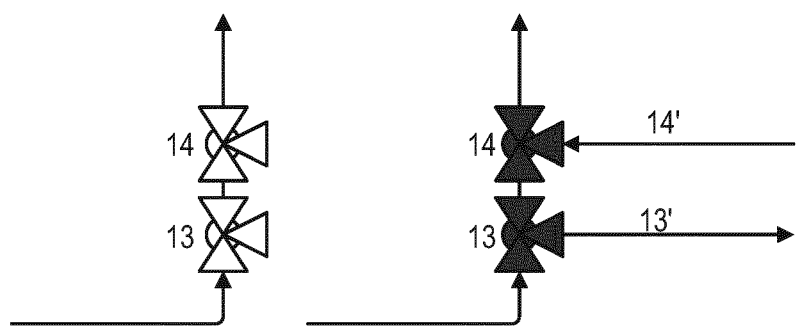
FIG. 3 shows the breather valve arrangement in the gas loop.

During normal measurement operation, the 3-way valves combination 13, 14, are not activated as illustrated in the left part of FIG. 3. This means gas simply flows through the valves 13,14 in a closed gas loop 10 with no connection with the outside environment. In order to flush the gas loop 10 with atmospheric air, both the 3-way valves 13,14 are activated simultaneously. When activated, the first 3-way valve 13 forces air coming from the membranes out of the air loop to the outside environment as shown in the right part of FIG. 3 and as illustrated with the arrow 13'. The second 3-way valve, 14 ensures that the suction force created by the air pump sucks in new air into the gas loop as illustrated with arrow 14' (FIG. 3).

Another important function of the CO2 probe is the ability to measure the entire carbonate buffer system concentration of a fish farm (primarily free CO2 and $HCO_3^-$). To do this acid is added to the water sample to measure any bound carbonate forms. As the sensor head is designed to read only free CO2 gas, a small dose of citric acid to the water sample (to <pH 4 or to pH<3 if H2S is also to be detected see further below), drives the carbonate buffer system completely to the left, ensuring nearly the entire buffer system becomes free CO2 gas. The final measurement is effectively the concentration of CO2 and HCO3— together.

Figure 4A:
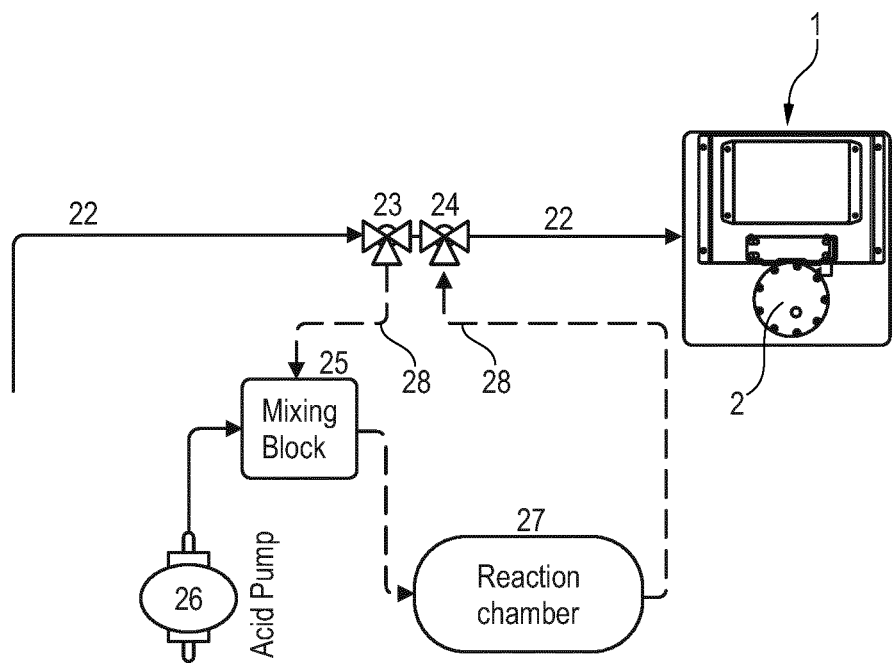
FIGS. 4a-4b show the sample preparation with acid addition for detection of dissolved carbonates and/or total carbonate content.
Figure 4B:
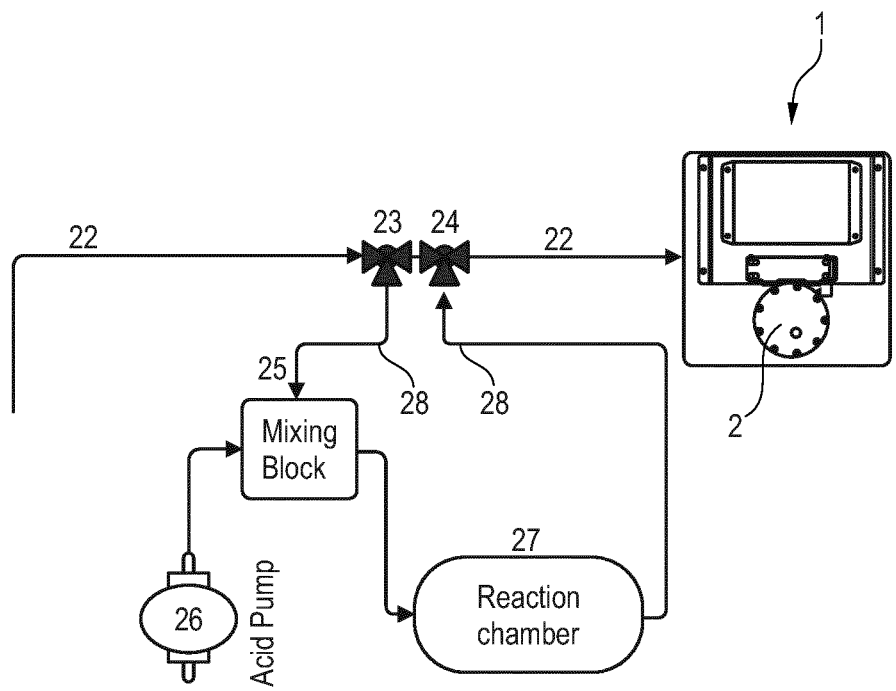

FIG. 4 illustrates the sample preparation for determination also of HCO3— concentration in the sample flow or thus the total carbonate content of the liquid sample. In order to force dissolved bicarbonate and carbonate ions to CO2 in gas form, pH is lowered to below pH 4 in the sample flow by addition of an acid. The acid is transferred from a not shown acid container.

When measuring the content of gaseous CO2 in the samples, the first and second bypass valves 23, 24 (FIG. 4*a*) remain deactivated. Thereby, the aqueous liquid sample can flow through the bypass valves 23, 24 and directly to the membrane block 2 of the CO2 detection and monitoring system 1. When the bypass valves 23, 24 are activated, the aqueous liquid sample is directed to a mixing block 25 FIG. 4*b*). When the bypass valves 23, 24 are activated an acid dosing pump 26 is also activated, delivering fine drops of acid, e.g. a citric acid solution, to the mixing block 25. Thereby pH of the aqueous liquid sample rapidly drops to below pH 4. The aqueous liquid sample enters a reaction chamber 27 to ensure a residence time that enables HCO3— to chemically shift from dissolved HCO3— to free CO2 gas. The acidified aqueous liquid sample is then directed to the CO2 membrane block 2 of the detection system 1.

In the CO2 and/or H2S detection system, the high level of free CO2 and/or H2S enables a rapid diffusion across the membranes in the membrane block 2 and ensures rapidly obtaining the equilibrium across the membranes when detecting total carbonate content in the acidified samples.

Figure 7A:
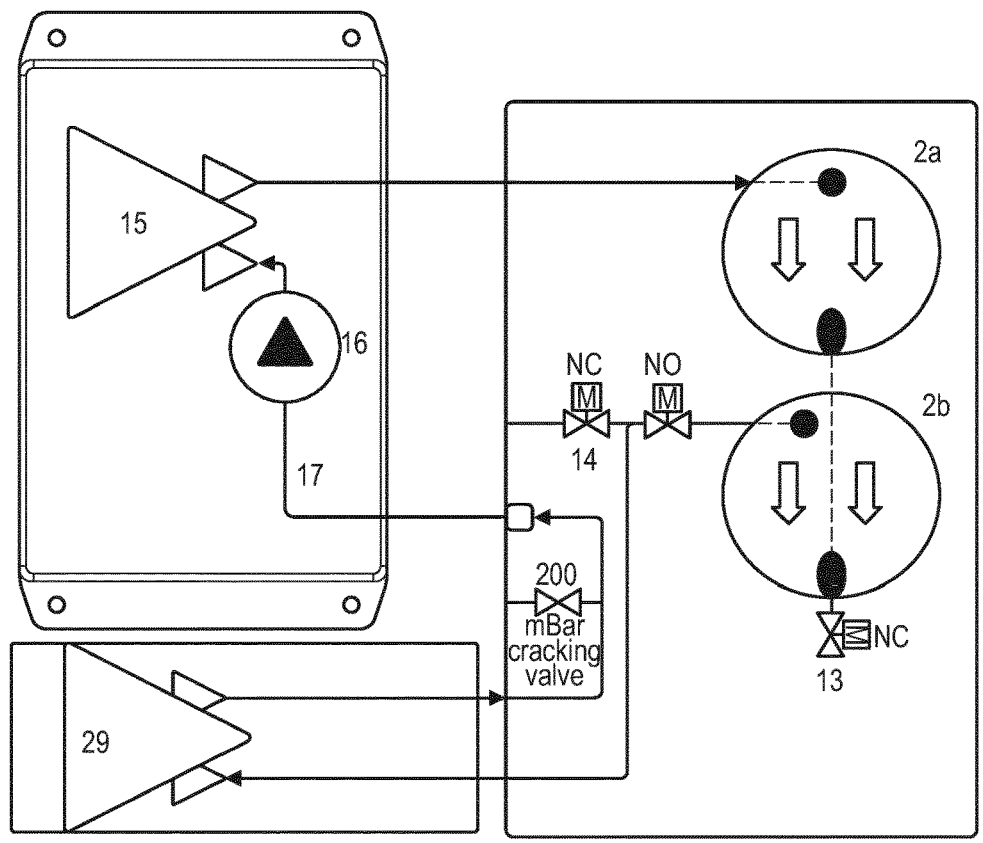
FIG. 7a shows a variant where the two membrane elements of the membrane blocks are arranged side by side arrangement.

FIG. 7*a* describes a variant of the membrane block, where the first and second membrane units 2*a*, 2*b* are arranged in a side-by-side manner. This allows for lower overall building height, easier access to the membrane chambers, e.g. for maintenance or re-pair, and for better condensation removal characteristics.

Figure 7B:
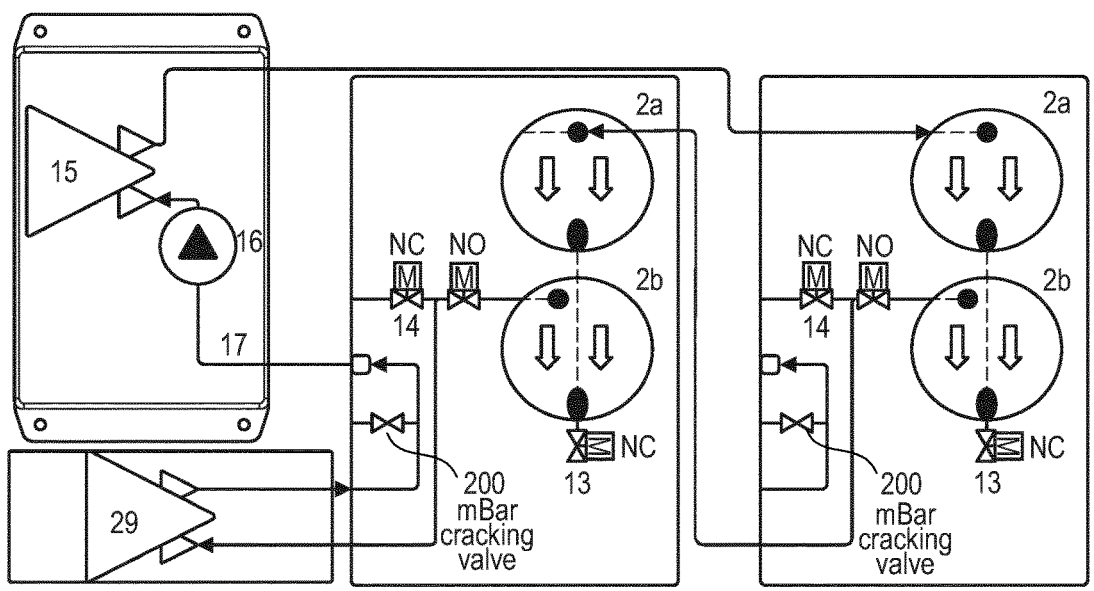
FIG. 7b shows a variant where the two membrane blocks are arranged each with their own air loop and sensors are applied in series.

Further, it is possible using two or more membrane blocks 2 in series, providing 4 membranes (or more) for gas separation rather than 2, see FIG. 7*b*.

Further, it is possible using two or more membrane blocks 2 in parallel, e.g. as discussed above when detecting CO2 gas with one detection and sampling unit while a second parallel detection unit receives acidified sample flow from the reaction chamber 27 so as to detect total carbonate content and/or H2S.

The entire process is controlled by a programmable logic controller (PLC). The PLC or another controller may also calculate the CO2, the total carbonate and/or dissolved carbonate and/or H2S concentration for further use, e.g. as a control parameter in a fish tank or pond in a land based fish farm.

EXAMPLES

Figure 2A:
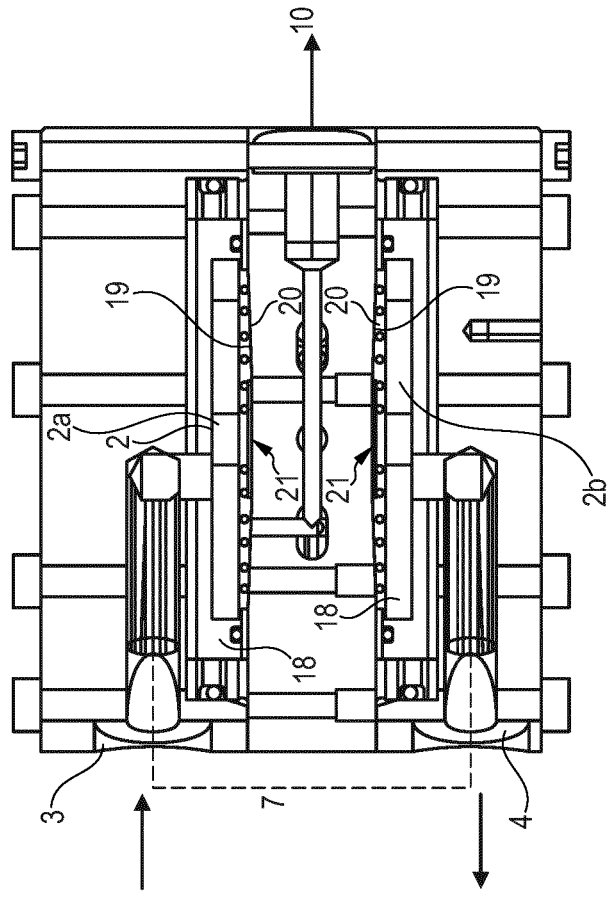
FIG. 2a is a cross sectional view of the membrane block of the system.

Several tests were made to assess the $CO_2$ detection system as shown in FIGS. 1-2. The same test sample was used for all tests: freshwater, 20° C.

The operating sequence up to and during a measurement was identical in all examples. The new CO2 detection system as shown in FIGS. 1-2 was used in all examples. When explicitly noted one membrane unit was disabled to perform comparative examples. The system with one membrane block disabled simulates commercially available CO2 detection systems.

Each of the tests in the examples were repeated in five identical test runs. In all tests an initial removal of free bubbles was performed using a closed container with an airspace in which free bubbles in the sample flow may be collected, and by extracting the sample from the bottom of the container.

In all examples a water sample flow of approx. 500 mL/min was used, The pressure in the liquid sample flow in all examples was raised to 200 mbar above atmospheric pressure on the liquid side of the membranes. All examples were conducted at ambient temperature, i.e. 21-22° C.

The air pressure in the air loop varied with the content of CO2 in the sample. Usually, the pressure in the air loop was only raised slightly above to atmospheric pressure during measurements and was between 20-60 mbar relative to atmospheric pressure, but may be quite variable depending on the CO2 content in the sample.

A PTFE membrane having a pore size of 0.02 microns was used in both membrane units in all examples. The membrane in each membrane unit was circular with a diameter of 76 mm.

Example 1

Comparing Two Membranes Versus One Membrane, in Relation to CO2 Gas Concentration in a Fresh Water Sample The new CO2 detection system as shown in FIGS. 1-2 with 2 membranes was initially tested (Graph 1, 2 membranes). Consistently a free CO2 gas content of 7 mg/L was achieved. Where the maximum CO2 concentration was evaluated to be 7 mg/L, a $T_{90}$ (time at which 90% of the total gas is measured) of about 4 minutes was possible.

The new free CO2 detection system as shown in FIGS. 1-2 with 1 membrane disabled was then tested (Graph 1, 1 membrane). This set-up would correspond to commercially available CO2 detection systems having a single membrane in membrane block which isolates gaseous CO2 from the liquid sample. A free CO2 gas content of between 5 and 6 mg/L was achieved. Where the maximum CO2 concentration was evaluated to be 7 mg/L, a $T_{90}$ about 7 minutes was possible.

Figure 5A:
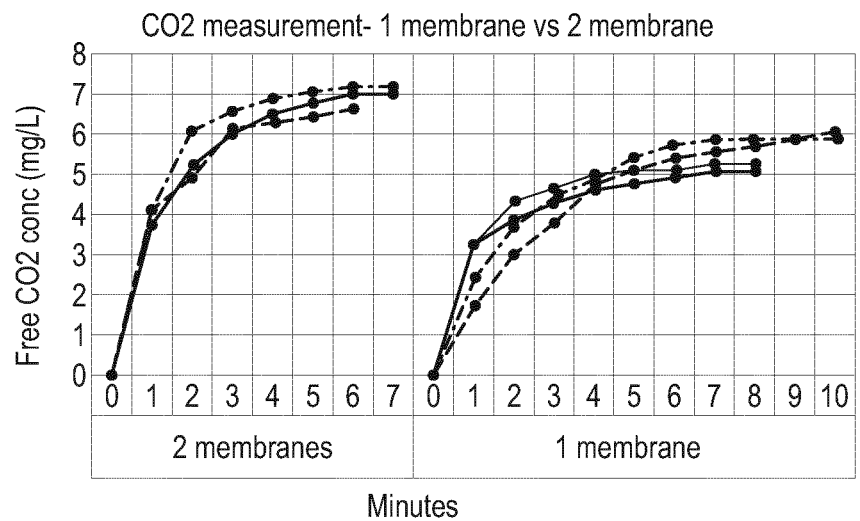
FIGS. 5a-c show graphs from the tests performed in examples 1-3.

FIG. 5a shows sample measuring time on the X-axis (in minutes) and the CO2 gas content detected by the sensor and computed into CO2 concentration (in mg/l) in the sample on the Y axis. Each line represents a repeated identical test run.

Test 2; 2 Membranes Versus 1 Membrane, dissolved HCO3— Concentration

The new free CO2 detection system as shown in FIGS. 1-2 with 2 membranes was initially tested (Graph 2, 2 membranes). Consistently a total of HCO3— content of 190 mg/L was achieved within 4-5 minutes.

The new free CO2 detection system as shown in FIGS. 1-2 with 1 membrane disabled was then tested (Graph 2, 1 membrane). A HCO3— content of a little over 80 mg/L was achieved after 12-13 minutes.

Figure 5B:
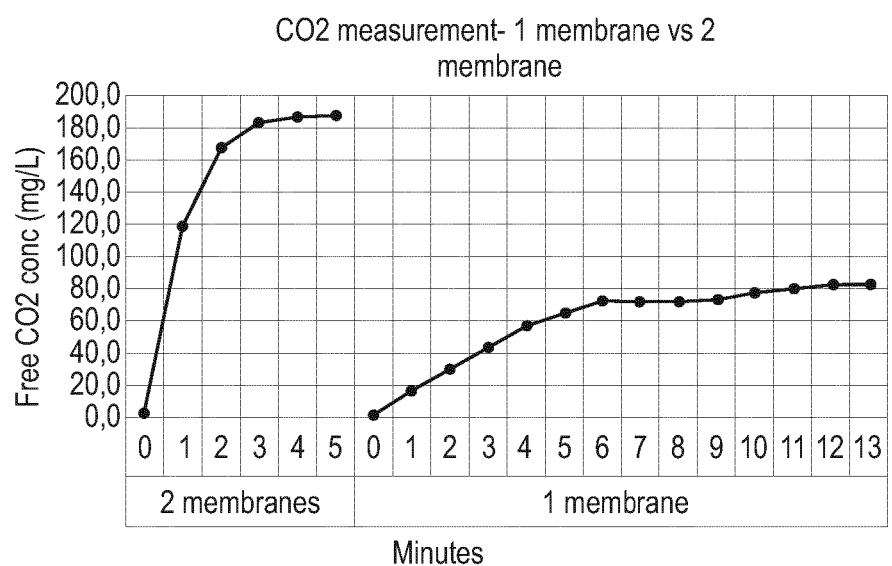

FIG. 5b shows sample measuring time on the X-axis (in minutes) and the CO2 gas content detected by the sensor and computed into total carbonate/CO2 concentration (in mg/l) in the sample on the Y axis.

Example 3

Standard Diffusion Time Between Measurements

The new free CO2 detection system as shown in FIGS. 1-2 with 1 membrane disabled was tested (FIG. 5c) for determining how long old sample air in the gas loop would need to diffuse across the membrane back to the sample water, driven by the gas partial pressure gradient towards equilibrium as per Henry's Law.

This test was made following a HCO3— measurement where the end concentration in the gas loop was high.

This test illustrated it would take about 5-6 minutes for the CO2 partial pressure in the air loop to drop to atmospheric levels, or corresponding to 0 mg/l in the sample flow and thus to be ready for a new measurement.

The detection system as shown in FIGS. 1-2, including membrane block, combined with the breather valve assembly for flushing old sample air from the air loop, can be at 0 mg/L in <5 seconds (corresponding the level of CO2 in atmospheric air).

Figure 5C:
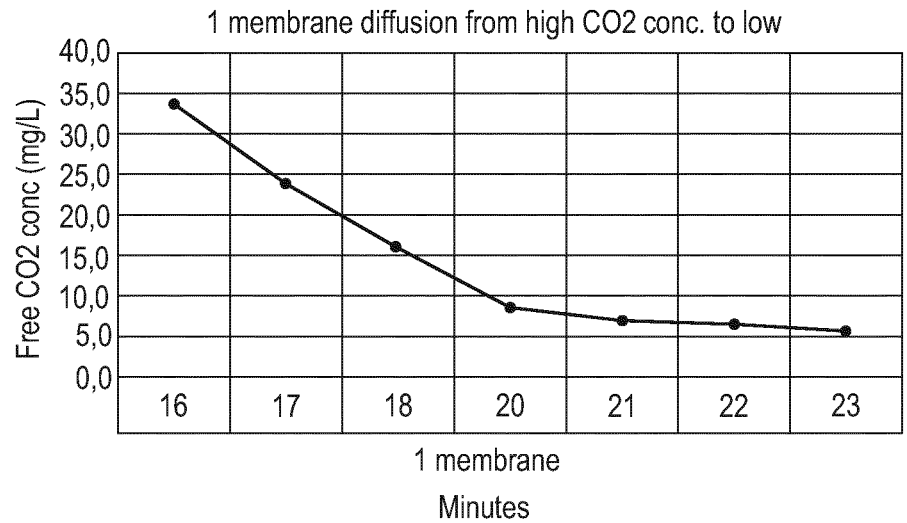

FIG. 5c shows sample measuring time on the X-axis (in minutes) and the CO2 gas content detected by the sensor and computed into CO2 concentration (in mg/l) in the sample on the Y axis.

Example 4

Comparing $H_2S$ Sensor Measurement Against Expected Concentrations

Several tests were made to assess the $H_2S$ detection system as shown in FIGS. 1-2 but with a H2S detection unit 29 as described above instead of the CO2 sensor 15.

The same test sample was used for all tests: freshwater, 20° C.

The operating sequence up to and during a measurement was identical in all examples and as described in examples 1-3 in relation to detection of CO2 in the setup with two membrane units in series.

Each of the tests in the examples were repeated in 2 identical test runs. In all tests an initial removal of free bubbles was performed using a closed container with an airspace in which free bubbles in the sample flow may be collected, and by extracting the sample from the bottom of the container.

In all examples a water sample flow of approx. 500 mL/min was used, the pressure in the liquid sample flow in all examples was raised to 200 mbar above atmospheric pressure on the liquid side of the membranes. All examples were conducted at ambient temperature, i.e. 18-20° C.

A PTFE membrane having a pore size of 0.02 microns was used in both membrane units in all examples. The membrane in each membrane unit was circular with a diameter of 76 mm.

A stock solution was made with 1 mg of $Na_2S$ in 20 L of distilled water. From this there was made three sample solutions with respectively 5, 10, 15 and 20 ml of stock solution mixed in 10 L of distilled water.

From this the actual $H_2S$ concentration in the sample solution can be calculated, these are the target values for the experiments. They can be seen in table 1, below

TABLE 1

| Sample solution(ml) | 5 | 10 | 15 | 20 |
|---|---|---|---|---|
| $H_2S$ concentration(μg/L) | 3.54 | 7.00 | 9.57 | 12.77 |

The experiment was performed by running the water sample past 2 membranes, letting the $H_2S$ diffuse across into the air loop and past the $H_2S$ sensor. Before the $H_2S$ in the sample could diffuse out of the water, it had to be warmed up to above 35° C. and have pH lowered to below 4. Warming the water sample was done with a heating element around the reaction chamber. Decreasing pH to below 4 was achieved by citric acid dosing.

Figure 9:
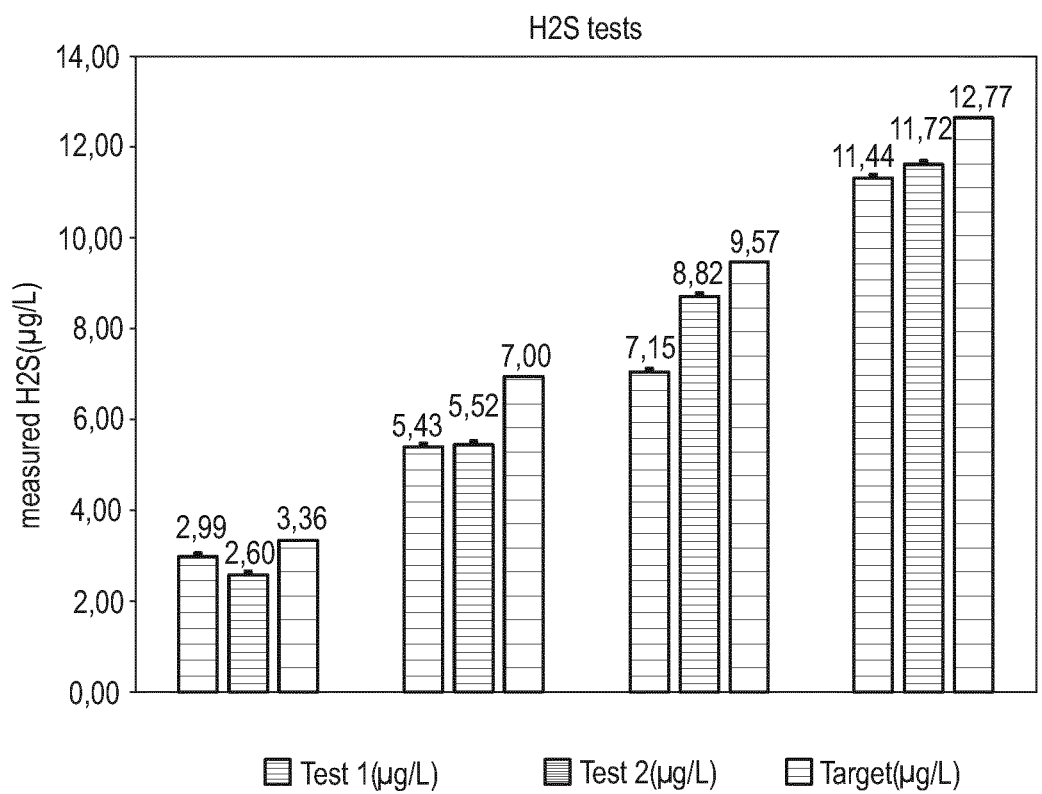

For each sample solution two duplicate experiments were performed. FIG. 6a shows the results from the experiment. There is a clear correlation between the target concentration of H2S (grey block in FIG. 8) and the H2S concentration level detected in the two parallel test runs (blue/orange blocks in FIG. 9)

REFERENCE NUMBERS

1. CO2 gas detection system
2. Membrane block
   a. First membrane unit
   b. Second membrane unit
3. Liquid sample inlet
4. Liquid sample outlet
5. Arrow indicating inlet flow
6. Arrow indicating outlet flow
7. Flow connection between first and second membrane units
8. Outlet of first membrane unit
9. Inlet on second membrane unit
10. Gas flow loop
11. Outlet of gas flow side of membrane block
12. Inlet of gas flow side of membrane block
13. First three-way valve in breather valve assembly
14. Second three-way valve in breather valve assembly
15. CO2 gas sensor (IR sensor)
16. Air pump
17. Air loop flow direction arrows
18. Liquid flow path
19. Membrane
20. Membrane support
21. Low height disc shaped chamber on gas flow side of membrane
22. Sample flow
23. First bypass valve
24. Second bypass valve
25. Mixing block
26. Acid pump
27. Reaction chamber
28. Bypass flow path for acidification of liquid sample
29. H2S detection unit
30. Sensor unit
31. transmitter unit
32. Distribution cap
33. Gas loop inlet in distribution cap
34. Gas loop outlet of distribution cap

What is claimed is:

1. A carbon dioxide or hydrogen sulphide sampling and detection system for determination of the content of gaseous carbon dioxide or hydrogen sulphide in an aqueous liquid, or for the detection of the total carbonate content in an aqueous liquid, wherein the sampling and detection system comprises:
   a membrane block including
      a liquid sample inlet port,
      a sample outlet port,
      a liquid sample flow path that extends between the liquid sample inlet port and the sample outlet port,
      a first membrane unit having a sample flow on a first side of a first permeable membrane element, and a carrier gas flow on a second side of the first permeable membrane element, and
      a second membrane unit having a sample flow on a first side of a second permeable membrane element and a carrier gas flow on a second side of the second permeable membrane element, and
   a carbon dioxide gas sensor or a hydrogen sulphide detection unit; and
   a gas circulation means;
   wherein said first and second membrane units are arranged in series in the liquid sample flow path; and
   wherein a gas flow path is a closed loop that includes the gas circulation means, the second side of the first membrane unit, the second side of the second membrane unit, and the carbon dioxide gas sensor or the hydrogen sulphide detection unit, and wherein the closed loop gas flow path further includes a breather valve arrangement with two serially connected three way valves between the carbon dioxide gas sensor or the hydrogen sulphide detection unit and atmosphere.

2. The system according to claim 1, wherein the carbon dioxide sensor is a sensor based on IR technology.

3. The system of claim 2, wherein the carbon dioxide gas sensor is configured and arranged to detect an absorption in the infra-red spectrum.

4. The system according to claim 1, wherein the hydrogen sulphide detection unit includes an electrochemical measuring cell with an electrolyte, a measuring electrode, a counter electrode and a reference electrode.

5. The system of claim 1, wherein the first and second membrane elements are hydrophobic membranes, the hydrophobic membranes are selected from the group consisting of: poly tetrafluorethylene membranes, poly dimethyl siloxane membranes and combinations thereof.

6. The system of claim 1, wherein the membrane elements have a pore size less than 0.02 microns.

7. The system of claim 1, further including a set of bypass valves and a bypass loop with a mixer station configured and arranged for admixing one or more acids into the liquid flow path.

8. The system of claim 1, wherein the system is configured and arranged to be portable.

9. The system of claim 1, wherein the system is configured and arranged to be operated in an in-line configuration within a fish farm.

10. The system of claim 1, wherein the sampling and detection system is configured to determine the gaseous content of gaseous carbon dioxide or hydrogen sulphide from a liquid broth.

11. A method for sampling and detection of carbon dioxide or hydrogen sulphide in a liquid, the method comprising the steps of:
   isolating gaseous carbon dioxide or hydrogen sulphide from the liquid in a membrane block by a sample flow liquid passing through the membrane block,
   bypassing the gaseous carbon dioxide or hydrogen sulphide contained in the sample flow through first and second permeable membrane elements in first and second membrane units of the membrane block and into a gas flow, while maintaining a sample liquid flow in the sample flow,
   where said first and second membrane units have the sample flow on the first side of first and second permeable membrane elements and a carrier gas flow on the second side of the first and second permeable membrane element, and said first and second membrane units are arranged in series in the liquid sample flow, and wherein the gas flow is a closed loop, and the gas is circulated through the membrane units and to a carbon dioxide gas sensor or a hydrogen sulphide detection unit arranged in the gas flow, and determining at least one of the content of gaseous carbon dioxide or hydrogen sulphide in the liquid, or detecting the total carbonate content in the liquid, wherein the gas flow includes a breather valve arrangement with two serial connected three-way valves arranged between the carbon dioxide gas sensor or the hydrogen sulphide detection unit and the gaseous side of the membrane block gas flow path, and further between the carbon dioxide gas sensor or the hydrogen sulphide detection unit and an air pump, and wherein the method further includes the steps of opening the breather valve arrangement between subsequent measurements for providing a connection from the gas flow path to ambient atmosphere, and allowing humidity to leave the carbon dioxide sensor or the hydrogen sulphide detection unit or for venting the gas present in the gas flow to the atmosphere prior to a subsequent measurement of carbon dioxide or hydrogen sulphide.

12. The method of claim 11, wherein the gas flow extends through the first and second membrane units in counter-current direction relative to the liquid sample flow.

13. The method of claim 11, wherein the gas flow extends through the first and second membrane units in concurrent direction relative to the liquid sample flow.

14. The method of claim 11, wherein the liquid is an aqueous liquid and further including the step of adding one or more acids to the aqueous liquid sample for setting free carbon dioxide from the aqueous liquid sample, prior to measuring the free carbon dioxide, and thereby obtaining a measure for the total carbonate concentration in the aqueous liquid sample.

15. The method of claim 11, characterized in, raising the temperature of the liquid sample flow to 25-45° C. or maintaining the temperature in the membrane block at 25-35° C.

16. The method of claim 11, wherein the liquid is an aqueous liquid.

17. The method of claim 11, further including raising the temperature of the liquid sample flow to around 30° C., or maintaining the temperature in the membrane block at around 30° C.

18. The method of claim 11, wherein the gas flow includes a breather valve arrangement with two serial connected three-way valves arranged between the carbon dioxide gas sensor or the hydrogen sulphide detection unit and a gaseous side of the membrane block gas flow path, and also further between an air pump and an air inlet to the membrane block, the method further including the steps of opening the breather valve arrangement between subsequent measurements for providing a connection from the gas flow path to ambient atmosphere, and allowing humidity to leave the carbon dioxide sensor or the hydrogen sulphide detection unit or for venting the gas present in the gas flow to the atmosphere prior to a subsequent measurement of carbon dioxide or hydrogen sulphide.

* * * * *